US00PP11116P

United States Patent [19]

Luby et al.

[11] Patent Number: Plant 11,116

[45] Date of Patent: Nov. 2, 1999

[54] STRAWBERRY PLANT NAMED 'MNUS 248'

[75] Inventors: James J. Luby, St. Paul; David K. Wildung, Grand Rapids, both of Minn.; Gene J. Galletta, Laurel, Md.

[73] Assignee: Regents of the University of Minnesota, Minneapolis, Minn.

[21] Appl. No.: 08/933,768

[22] Filed: Sep. 19, 1997

[51] Int. Cl.[6] ..... A01H 5/00

[52] U.S. Cl. ..... Plt./48

[58] Field of Search ..... Plt./48

*Primary Examiner*—Elizabeth Kemmerer

*Attorney, Agent, or Firm*—Mueting, Raasch & Gebhardt, P.A.

[57] ABSTRACT

A new and distinct variety of Junebearing strawberry plant named MNUS 248 combines the characteristics of midseason ripening, high productivity or yield, excellent survival in cold temperatures, resistance to red stele root rot, and moderate resistance to common foliar diseases. MNUS 248 yields strawberries characterized by a flavor that is balanced between sweetness and acidity, a glossy appearance, a firm flesh with a melting, creamy texture in the mouth.

4 Drawing Sheets

BACKGROUND OF THE INVENTION

MNUS 248 is a Junebearing or short-day strawberry variety (*Fragaria×ananassa*) that is notable for its combination of traits that include a midseason ripening period; high productivity or yield; excellent survival in cold temperatures; resistance to five Eastern North American races of *Phytophthora fragariae* Hickman, the causal organism of red stele root rot; moderate resistance to common foliar diseases such as leaf spot, powdery mildew and leaf scorch; and a fruit with a smooth, creamy texture.

BRIEF DESCRIPTION OF THE PHOTOGRAPHS

The accompanying photographs are typical specimens of the plants of the variety and the fruit thereof as depicted in color. The plants and fruit illustrated were grown at the University of Minnesota West Central Experiment Station at Morris, Minn. in July 1995. References to color relate to The Royal Horticultural Society Colour Chart, 1996 edition, noted herein as R.H.S. except for color terms of ordinary dictionary meaning which may occasionally be referred to.

Figure 1:
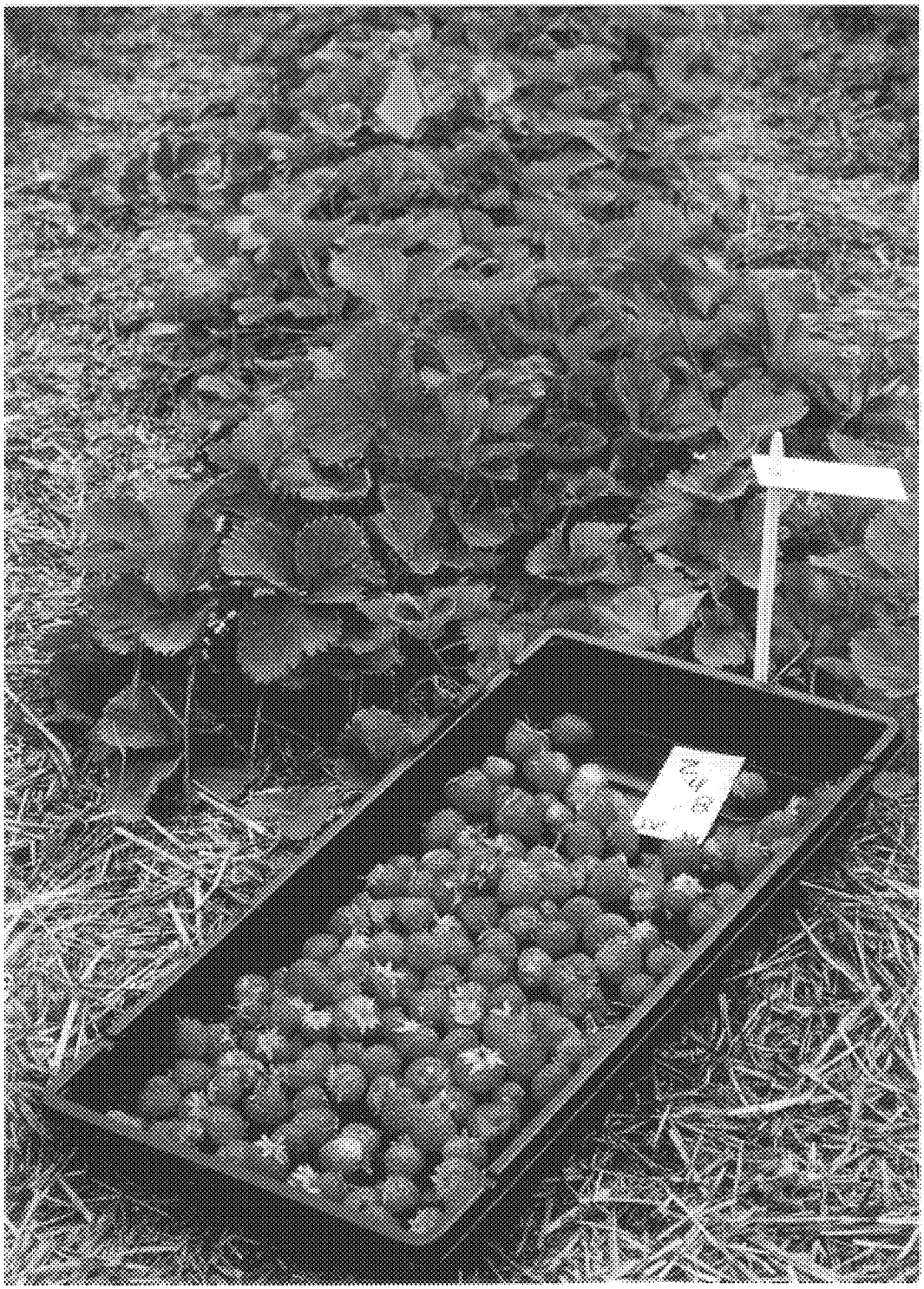
FIG. 1 is a photograph of a row of plants of the variety showing the typical growth habit behind a tray of typical fruit as harvested.
Figure 2:
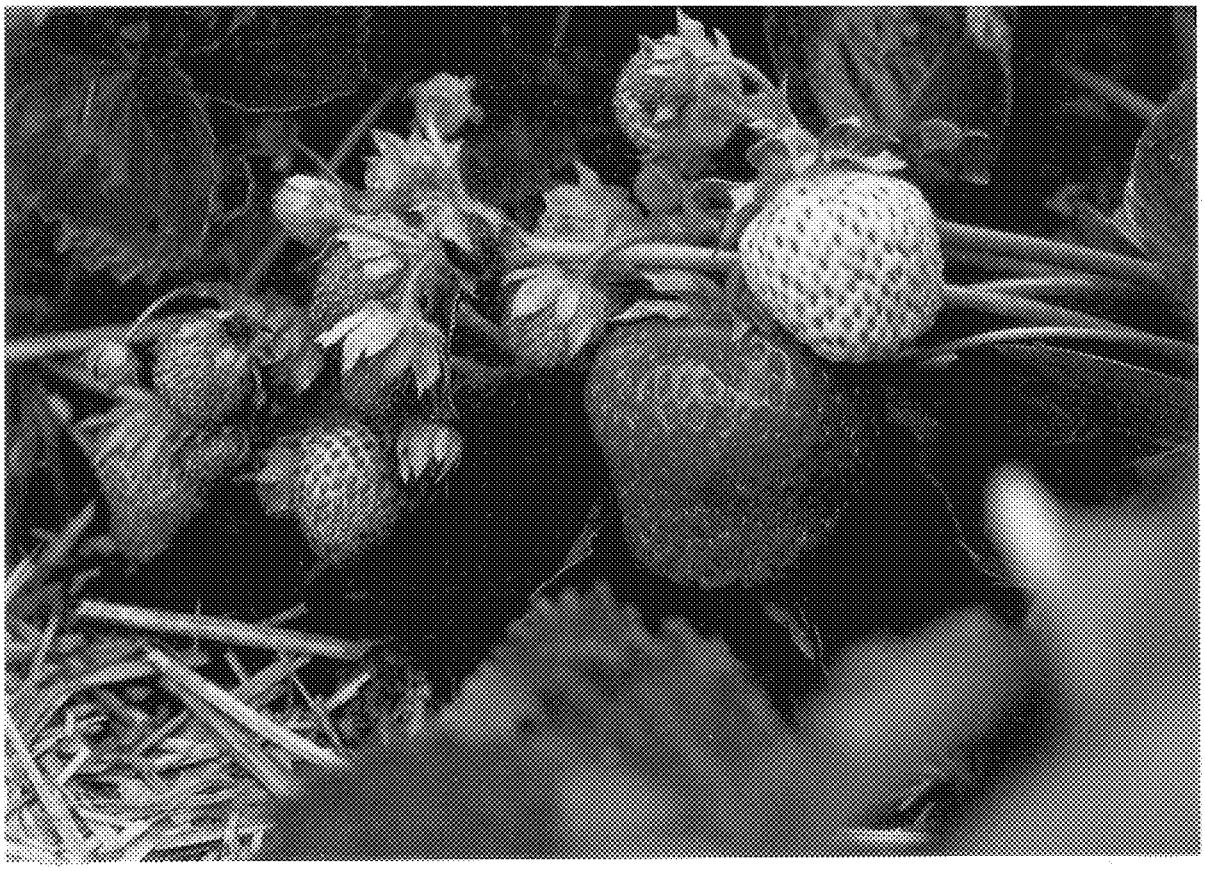
FIG. 2 is a photograph of a cluster of fruit of the variety showing several stages of maturity.
Figure 3:
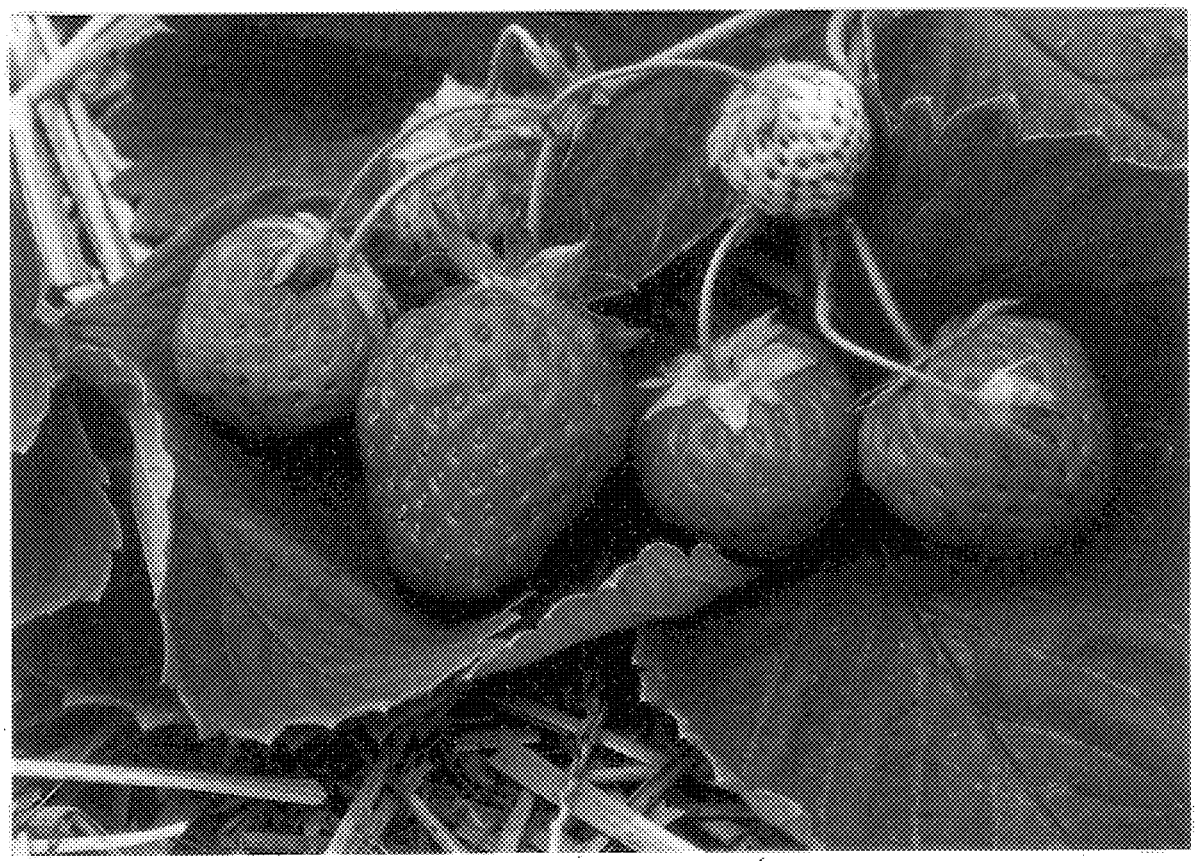
FIG. 3 is a photograph of a cluster of fruit of the variety showing mostly fully ripened fruit.
Figure 4:
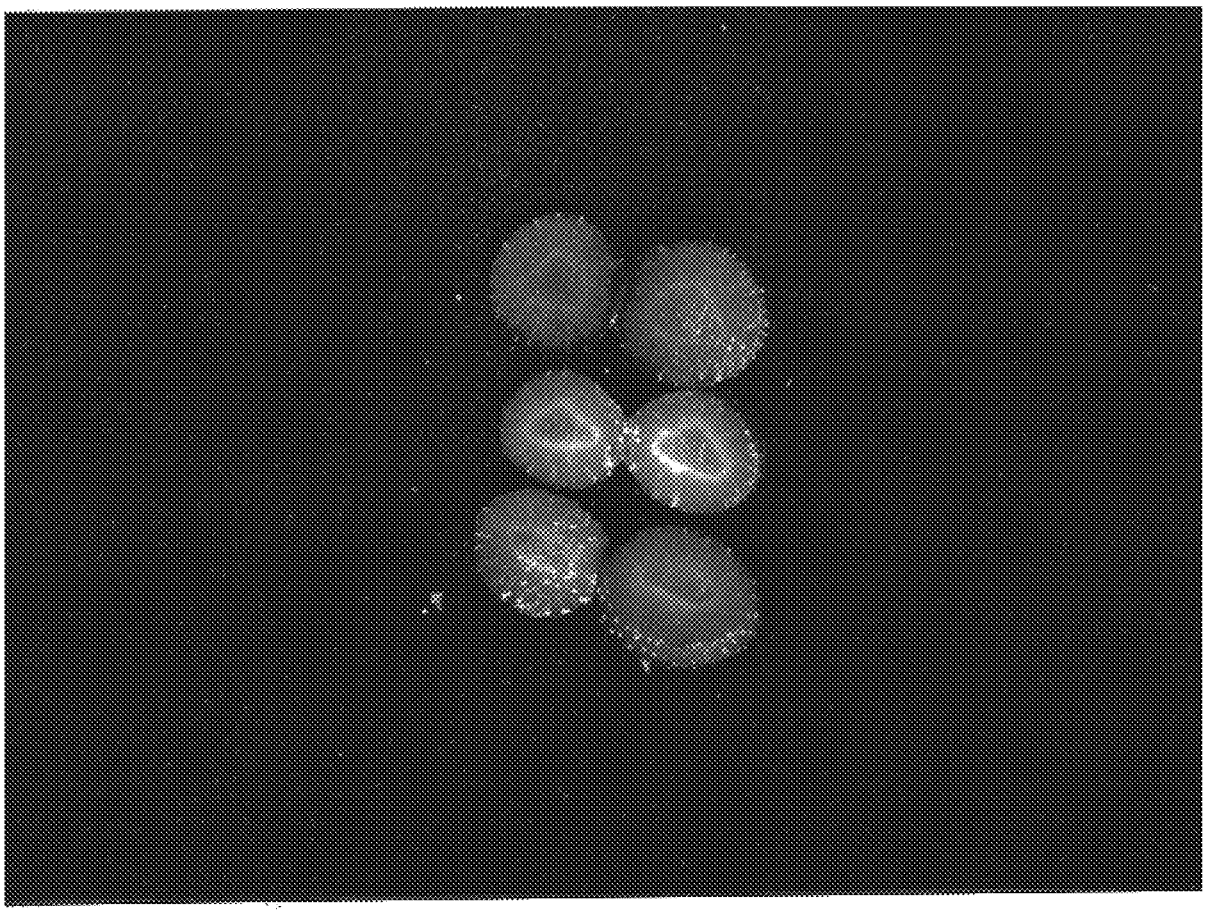
FIG. 4 is a photograph of several sliced ripe fruit showing the internal coloring of the fruit.

Following is a detailed description or specification of the present variety.

Origin of the Variety

MNUS 248 is a result of a cross between Glooscap and an unnamed seedling designed MNUS 99, made in a controlled breeding program in 1986 at Beltsville, Md. MNUS 248 was discovered and selected at the University of Minnesota North Central Experiment Station at Grand Rapids, Minn. in 1988. The variety has been stable and uniform through propagation by stolons and by in vitro micropropagation from stolon meristems. Off-types, variants, and mutations have not been observed. MNUS 248 was propagated by stolons for later observation in trails at the University of Minnesota Horticultural Research Center near Excelsior, Minn. and the North Central Experiment Station at Grand Rapids, Minn. from 1989 to 1990, and at the USDA Beltsville Agricultural Research Center, Beltsville, Md. in 1991 and in 1996.

MNUS 248 was evaluated in replicated yield trials from 1992 through 1996 at The Horticultural Research Center, the North Central Experiment Station, and the West Central Experiment Station at Morris, Minn. (Tables 1 through 12). At each site, plantings were estabished in 1991, 1993 and 1995 and harvested for one or two subsequent seasons. MNUS 248 and other common cultivars of the midwestern U.S. and eastern Canada were planted in a randomized complete block design. Plants were spaced 0.45 m apart within rows that were 1.2 m apart and 4 m long. The plants were permitted to form a matted row that was approximately 0.4 m wide. At Grand Rapids, a split plot design was employed on 7 m long plots which were split with half of the plot being mulched for protection during the winter and the other half receiving no mulch. All plots were irrigated, fertilized, and sprayed with fungicide and insecticide as needed in accordance with standard commercial recommendations.

Detailed Description of the Variety

Fruit: The fruit of MNUS 248 matures in the middle part of the fruiting season for short day varieties. The fruit matures approximately at the same time as fruit of the cultivars Glooscap, Kent, Cavendish, and Jewel which are commonly grown in Minnesota (Tables 1, 2, 3 and 4). Compared to these varieties, the berries of MNUS 248 generally have been similar in size to those of Glooscap and Kent and smaller than those of Cavendish and Jewel (as measured by average berry weight; Tables 1, 2, 3 and 4). Subjective comparisons of the fruit characteristics of MNUS 248 with other adapted varieties are presented in Tables 5, 6, 7, 8 and 9. The flavor is well balanced between sugars and acids with a characteristic strawberry aroma. The flesh is moderately firm with a consistent, creamy, melting mouthfeel. The skin is of medium toughness but tends to become weak in hot weather. The fruit of MNUS 248 have a glossy skin with slightly uneven deep crimson skin color corresponding to R.H.S. Colour Chart plate 53A in lighter areas and 185A in darker areas. The skin does not tend to darken as much as Glooscap. The flesh color is fairly uniform dark red through the fruit and corresponds to R.H.S. Colour Chart plate 34A except for a whitish vascular cylinder. The surface of the fruit is smooth to slightly uneven. The shape is blunt-wedge or blunt-conic with large shoulders on primary berries to blunt-conic on the secondary and tertiary berries. The berries are equaal in length and width to slightly longer than broad. The peduncle is medium to long in length and prostrate by the time of the first harvest. The calyx is equal in diameter to the fruit, showy, inserted in a shallow basin, and clasping to partially reflexed. Sepals are borne in two whorls with the inner whorl being elliptic with sharp points, and the outer whorl being narrow lanceolate with rounded tips. The achenes are yellow and below the surface of the fruit and are absent from only a narrow band at the calyx end of the fruit.

Flowers: The inflorescence is usually slightly below or level with the foliage when the flowers are open. The flower size is medium. The diameter of the calyx is similar to or larger than the diameter of the corolla. The diameter of the inner calyx is similar to the diameter of the outer calyx. Secondary flowers have five petals which tend to be greater in breadth than in length and these are free or touching but usualy not greatly overlapping one another. The color of the petal corresponds to plate 155C of The R.H.S. Colour Chart.

Plants: Plants of MNUS 248 have crowns that are medium in height with many petioles and usually form a matted row of high plant density and flat to flat-globose habit. Stolons are thin and green proximal to the mother plant and, distally, take on a slight red anthocyann coloration. Stolons may have bracts at the blind nodes. Pubescence on the stolons is sparse to moderate in density and spreading.

Leaves: The leaves have medium to short petioles giving the appearance of a flat-globose to globose canopy. Pubescence on the petioles is sparse and spreading (divaricate). Petiolules may be present on the petiole. The leaves have three leaflets with medium roughness from interveinal blisters and sparse pubescence on the adaxial side of the leaflets, primarily on top of veins. Leaflets are equal in size, broadly elliptic, sparsely pubescent, medium green on top, light green on the bottom with prominent veins. The leaflets of MNUS 248 have a slight waxy bloom on the upper side giving a slightly bluish-green cast. The color of the terminal leaflet corresponds to R.H.S. Colour Chart 146A on the upper side and 147C on the lower side. The terminal leflet is equal in length and width, has a flat to cupped profile, a rounded base, and single teeth that are obtuse on older leaves. Stipules are small to medium in size and pointed.

Fruiting: Results are pesented in Tables 1, 2, 3 and 4 from replicated trials conducted at three Uniersity of Minnesota experiment station sites in Minnesota: The Horticultural Research Center near Excelsior, the North Central Experiment Station at Grand Rapids, and the West Central Experiment Station at Morris. MNUS 248 has generally produced high yields and medium-large berries in trils in Minnesota. The fruit matures in the middle part of the season for short-day cultivars, approximately at the same time as its parent, Glooscap, and other common midseason cultivars grown in Minnesota such as Kent, Jewel and Cavendish. In all trials in Minnesota, MNUS 248 consistently had yields similar to or greater than these other mid-season varieties. Glooscap, a parent of MNUS 248, is currently to most widely planted midseason cultivar among commercial Minnesota producers. MNUS 248 had a higher yield than Glooscap in 16 of 19 trials and a greater average berry weight in 17 of 19 trials. MNUS 248 has been productive on soils of heavy and light texture in matted row production systems. It has had limited testing in hill systems.

Responses to diseases and stresses: Relative to other cultivars tested in Minnesota, MNUS 248 has moderate resistance to the common foliar diseases, leaf spot (*Mycosphaerella fragariae* Tul.) and powdery mildew (*Sphaerotheca macularis* Walls ex Fr.) and moderate to high resistance to leaf scorch (*Diplocarpon earliana* Ell. and Ev.) (Tables 10, 11 and 12). MNUS 248 is resistant to five eastern North American races of *Phytophthora fragariae* Hickman (Races A-1, A-2, A-3, A-4 and A-6), the fungus that causes red stele root rot (Table 13). It is moderately tolerant, relative to other cultivars tested, of black root rot-causing organisms, Rhizoctonia spp. and Pythium spp. based on field observations in The Horticultural Research Center, Excelsior, MN (Table 11). Plants of MNUS 248 seldom have exhibited symptoms of winter injury in Minnesota trials and have been among the most hardy of varieties and selections tested (as indicated by plant stand, winter stand loss and vigor ratings in Tables 1,2,3 and 4; and winter injury ratings in Table 11). Thus, it is particularly hardy in temperatures to about −40° C., typical of the United States Department of Agriculture Zone Hardiness 3 and 4.

TABLE 1

Performance of strawberry cultivars at the University of Minnesota North Central Experiment Station, Grand Rapids, Minnesota in 1992–1995.[1]

| Cultivar | Mulched | | Unmulched | | Mulched | | Unmulched | |
|---|---|---|---|---|---|---|---|---|
| | Yield (1000 lb/A) | | | | Berry weight (g) | | | |
| | 1992 | 1993 | 1992 | 1993 | 1992 | 1993 | 1992 | 1993 |
| Annapolis | 12.2 | 9.1 | 9.9 | 7.8 | 16.2 | 13.0 | 13.9 | 10.9 |
| Veestar | 6.8 | 8.2 | 7.3 | 7.3 | 11.1 | 6.9 | 9.1 | 6.8 |
| Honeoye | 12.0 | 11.8 | 12.3 | 13.7 | 16.1 | 13.2 | 14.1 | 10.3 |
| MNUS 248 | 17.8 | 22.2 | 17.1 | 21.5 | 15.2 | 13.6 | 13.7 | 13.3 |
| Glooscap | 11.0 | 11.9 | 8.0 | 10.0 | 13.7 | 11.6 | 12.1 | 12.0 |
| Kent | 21.4 | 18.5 | 19.0 | 17.9 | 15.7 | 13.1 | 14.2 | 11.8 |
| Cavendish | 15.6 | 14.8 | 10.6 | 17.2 | 18.9 | 14.1 | 16.8 | 9.6 |
| Trumpeter | 16.5 | 14.3 | 12.8 | 13.0 | 13.0 | 11.0 | 13.1 | 10.8 |
| Northland | 16.8 | 19.9 | 14.3 | 20.1 | 14.3 | 11.6 | 13.7 | 10.5 |
| MNUS 210 | 16.0 | 13.7 | 17.2 | 17.0 | 21.3 | 14.8 | 18.5 | 14.3 |
| Blomidon | 7.7 | 7.4 | 5.1 | 8.5 | 13.1 | 10.1 | 12.5 | 9.1 |
| Lateglow | 9.8 | 7.3 | 11.4 | 9.0 | 19.2 | 15.5 | 16.4 | 12.5 |
| Bounty | 16.4 | 13.9 | 13.8 | 20.5 | 14.8 | 11.9 | 12.1 | 10.8 |
| LSD 5% | 3.9 | 4.3 | 4.9 | 5.8 | 2.9 | 1.9 | 2.7 | 2.0 |
| | 1994 | 1995 | 1994 | 1995 | 1994 | 1995 | 1944 | 1995 |
| Veestar | 6.2 | 9.2 | 6.7 | 7.9 | 8.6 | 6.2 | 9.6 | 7.0 |
| Annapolis | 5.0 | 8.7 | 4.8 | 8.5 | 13.7 | 10.7 | 12.9 | 9.0 |
| Honeoye | 2.6 | 8.3 | 3.1 | 10.0 | 10.6 | 8.4 | 11.5 | 8.0 |
| Chambly | 1.9 | 7.8 | 1.5 | 5.9 | 10.1 | 7.8 | 14.9 | 8.2 |
| Earliglow | 2.2 | 2.7 | 2.0 | 3.4 | 9.5 | 6.2 | 11.0 | 6.9 |
| MNUS 248 | 6.1 | 14.1 | 7.5 | 11.3 | 14.9 | 11.0 | 12.0 | 11.3 |
| Glooscap | 8.2 | 11.4 | 9.5 | 13.7 | 12.0 | 8.5 | 13.2 | 8.6 |
| Kent | 5.4 | 5.8 | 6.1 | 7.0 | 11.4 | 8.9 | 15.1 | 8.7 |
| Cavendish | 5.4 | 5.6 | 5.9 | 6.3 | 14.7 | 9.2 | 15.3 | 12.4 |
| Jewel | 5.9 | 7.4 | 6.3 | 5.0 | 10.8 | 11.3 | 12.2 | 11.3 |
| Seneca | 3.2 | 4.9 | 3.6 | 2.6 | 9.8 | 9.8 | 12.8 | 9.0 |
| Blomidon | 3.0 | 2.1 | 4.3 | 1.5 | 7.9 | 8.2 | 13.4 | 7.8 |
| MNUS 210 | 9.0 | 5.5 | 7.9 | 7.8 | 13.9 | 12.1 | 10.2 | 11.9 |
| Lateglow | 4.4 | 3.9 | 4.7 | 3.9 | 14.5 | 9.3 | 12.3 | 9.1 |
| LSD 5% | 2.3 | 3.1 | 3.4 | 4.4 | 1.7 | 1.9 | 2.0 | 2.3 |
| | % Early harvest[2] | | | | Stand (%)[3] | | | |
| | 1992 | 1993 | 1992 | 1993 | 1992 | 1993 | 1992 | 1993 |
| Annapolis | 57 | 56 | 79 | 76 | 97 | 94 | 97 | 93 |
| Veestar | 58 | 41 | 74 | 59 | 89 | 74 | 92 | 99 |
| Honeoye | 22 | 36 | 54 | 49 | 93 | 90 | 94 | 76 |
| MNUS 248 | 39 | 24 | 60 | 36 | 95 | 95 | 95 | 95 |
| Glooscap | 28 | 27 | 57 | 50 | 86 | 79 | 84 | 88 |
| Kent | 16 | 28 | 46 | 51 | 99 | 98 | 96 | 95 |

TABLE 1-continued

Performance of strawberry cultivars at the University of Minnesota North Central Experiment Station, Grand Rapids, Minnesota in 1992–1995.[1]

| Cultivar | Mulched | | Unmulched | | Mulched | | Unmulched | |
|---|---|---|---|---|---|---|---|---|
| Cavendish | 21 | 27 | 54 | 52 | 92 | 81 | 90 | 85 |
| Trumpeter | 28 | 21 | 61 | 50 | 96 | 96 | 95 | 98 |
| Northland | 25 | 25 | 56 | 50 | 95 | 91 | 93 | 91 |
| MNUS 210 | 4 | 16 | 16 | 41 | 97 | 71 | 99 | 96 |
| Blomidon | 18 | 16 | 36 | 30 | 94 | 75 | 91 | 81 |
| Lateglow | 7 | 9 | 30 | 38 | 94 | 89 | 94 | 93 |
| Bounty | 1 | 3 | 14 | 10 | 97 | 99 | 97 | 91 |
| LSD 5% | 11 | 12 | 17 | 16 | 10 | 26 | 17 | 23 |
| | 1994 | 1995 | 1994 | 1995 | 1994 | 1995 | 1944 | 1995 |
| Veestar | 75 | 70 | 78 | 80 | 88 | 93 | 90 | 95 |
| Annapolis | 57 | 61 | 84 | 76 | 85 | 90 | 85 | 90 |
| Honeoye | 56 | 58 | 68 | 67 | 64 | 88 | 61 | 88 |
| Chambly | 40 | 62 | 75 | 71 | 48 | 87 | 35 | 70 |
| Earliglow | 49 | 53 | 49 | 70 | 74 | 85 | 49 | 85 |
| MNUS 248 | 36 | 31 | 42 | 35 | 66 | 90 | 86 | 85 |
| Glooscap | 20 | 38 | 32 | 37 | 84 | 80 | 89 | 92 |
| Kent | 31 | 39 | 48 | 46 | 86 | 65 | 61 | 48 |
| Cavendish | 36 | 31 | 50 | 40 | 74 | 60 | 80 | 80 |
| Jewel | 15 | 35 | 30 | 51 | 93 | 85 | 84 | 77 |
| Seneca | 30 | 32 | 42 | 62 | 69 | 67 | 76 | 70 |
| Blomidon | 3 | 28 | 21 | 50 | 80 | 57 | 78 | 50 |
| MNUS 210 | 3 | 9 | 13 | 16 | 90 | 93 | 100 | 80 |
| Lateglow | 15 | 13 | 75 | 25 | 80 | 88 | 75 | 80 |
| LSD 5% | 14 | 18 | 14 | 13 | 20 | 26 | 22 | 29 |

[1]Plantings established in 1991 and 1993 and harvested in the subsequent two years.
[2]% Early harvest = % of total crop harvested from 7/02/92 to 7/13/92 (full season 7/02/92 to 8/05/92); 7/02/93 to 7/12/93 (full season 7/02/93 to 8/02/93); 6/23/94 to 7/1/94 (full season 6/23/94 to 7/22/94); and 6/26/95 to 6/29/95 (full season 6/26/95 to 7/21/95).
[3]% Stand was evaluated during June of each year.

TABLE 2

Peformance of strawberry cultivars at the West Central Experiment Station, Morris, Minnesota, in 1992–1995.[1]

| Cultivar | Yield (1000 lb/A) | | Berry weight (g) | | % Early harvest[2] | |
|---|---|---|---|---|---|---|
| | 1992 | 1993 | 1992 | 1993 | 1992 | 1993 |
| Veestar | 3.3 | 3.7 | 6.4 | 8.2 | 61 | 65 |
| Annapolis | 6.8 | 4.7 | 10.0 | 10.4 | 49 | 46 |
| Honeoye | 5.5 | 8.9 | 15.4 | 12.5 | 18 | 24 |
| Redcoat | 12.9 | 9.3 | 9.5 | 10.7 | 26 | 31 |
| MNUS 248 | 12.4 | 13.0 | 10.8 | 11.7 | 20 | 18 |
| Glooscap | 4.9 | 6.4 | 9.4 | 9.5 | 30 | 22 |
| Kent | 10.5 | 11.7 | 12.4 | 13.9 | 26 | 27 |
| Cavendish | 9.0 | 9.1 | 12.6 | 15.9 | 31 | 19 |
| Jewel | 5.5 | 3.8 | 10.0 | 11.2 | 26 | 37 |
| Trumpeter | 7.6 | 9.2 | 13.4 | 9.5 | 5 | 15 |
| MNUS 210 | 12.0 | 10.5 | 17.4 | 15.0 | 13 | 3 |
| Blomidon | 9.9 | 7.9 | 11.1 | 12.6 | 3 | 4 |
| Lateglow | 12.0 | 8.0 | 16.0 | 11.2 | 0 | 1 |
| Bounty | 6.1 | 4.7 | 11.8 | 8.5 | 2 | 5 |
| LSD 5% | 3.7 | 3.0 | 3.5 | 1.5 | 12 | 10 |
| | 1994 | 1995 | 1994 | 1995 | 1994 | 1995 |
| Veestar | 14.5 | 9.6 | 6.9 | 7.4 | 54 | 75 |
| Earliglow | 8.2 | 3.8 | 6.3 | 6.3 | 44 | 72 |
| Annapolis | 11.5 | 7.8 | 9.3 | 9.4 | 37 | 61 |
| Honeoye | 15.1 | 10.7 | 10.6 | 9.3 | 25 | 53 |
| Chambly | 9.6 | 6.2 | 8.3 | 7.1 | 20 | 42 |
| MNUS 248 | 16.4 | 18.2 | 9.9 | 9.3 | 8 | 28 |
| Glooscap | 13.9 | 15.4 | 10.2 | 9.1 | 10 | 42 |
| Kent | 17.0 | 11.7 | 10.0 | 9.4 | 23 | 29 |
| Cavendish | 19.6 | 15.4 | 12.5 | 13.7 | 18 | 17 |

TABLE 2-continued

Peformance of strawberry cultivars at the West Central Experiment Station, Morris, Minnesota, in 1992–1995.[1]

| | | | | | | |
|---|---|---|---|---|---|---|
| Jewel | 14.3 | 11.9 | 12.3 | 11.7 | 4 | 17 |
| Seneca | 11.7 | 10.3 | 11.7 | 10.4 | 12 | 25 |
| Blomidon | 6.7 | 8.3 | 9.2 | 10.5 | 4 | 6 |
| Lateglow | 6.1 | 4.6 | 7.4 | 8.5 | 0 | 18 |
| MNUS 210 | 5.6 | 6.3 | 9.6 | 8.2 | 0 | 18 |
| LSD 5% | 3.6 | 4.4 | 1.6 | 1.6 | 11 | 14 |

| Cultivar | % Stand[3] | | Vigor[4] | | Winter Stand loss[5] (%) | |
|---|---|---|---|---|---|---|
| | 1992 | 1993 | 1992 | 1993 | 1992 | 1993 |
| Veestar | 80 | 73 | 7.5 | 7.5 | n.a. | −8 |
| Annapolis | 80 | 73 | 7.8 | 7.0 | n.a. | −8 |
| Honeoye | 88 | 83 | 8.8 | 8.8 | n.a. | −13 |
| Redcoat | 88 | 93 | 8.8 | 7.5 | n.a. | −5 |
| MNUS 248 | 73 | 73 | 7.8 | 6.2 | n.a. | −5 |
| Glooscap | 70 | 58 | 6.8 | 6.2 | n.a. | −15 |
| Kent | 78 | 70 | 8.8 | 6.8 | n.a. | 0 |
| Cavendish | 80 | 75 | 7.8 | 7.5 | n.a. | −5 |
| Jewel | 75 | 63 | 8.0 | 7.2 | n.a. | −18 |
| Trumpeter | 88 | 83 | 8.5 | 8.2 | n.a. | −12 |
| MNUS 210 | 70 | 68 | 7.8 | 7.8 | n.a. | −5 |
| Blomidon | 85 | 73 | 8.5 | 7.5 | n.a. | −10 |
| Lateglow | 88 | 85 | 8.5 | 8.2 | n.a. | −5 |
| Bounty | 83 | 80 | 8.8 | 7.2 | n.a. | −15 |
| LSD 5% | 16 | 21 | 1.2 | 1.6 | | 12 |
| | 1994 | 1995 | 1994 | 1995 | 1994 | 1995 |
| Veestar | 98 | 88 | 9.0 | 8.3 | 0 | 5 |
| Earliglow | 85 | 70 | 8.3 | 8.0 | −15 | 0 |
| Annapolis | 83 | 65 | 8.0 | 7.5 | −10 | 0 |
| Honeoye | 88 | 70 | 7.8 | 7.8 | 0 | 3 |
| Chambly | 80 | 48 | 7.3 | 6.3 | −13 | −8 |
| MNUS 248 | 100 | 80 | 8.5 | 6.8 | 0 | −5 |
| Glooscap | 85 | 85 | 8.0 | 8.0 | −5 | 5 |
| Kent | 80 | 55 | 7.5 | 7.3 | −8 | −3 |
| Cavendish | 95 | 83 | 8.5 | 8.3 | 3 | −3 |
| Jewel | 98 | 73 | 9.0 | 8.3 | 0 | 0 |
| Seneca | 80 | 63 | 8.3 | 8.0 | −13 | −5 |
| Blomidon | 93 | 78 | 7.8 | 7.3 | −8 | −5 |
| Lateglow | 88 | 63 | 7.0 | 6.8 | −13 | 3 |
| MNUS 210 | 93 | 25 | 7.5 | 6.0 | −8 | −18 |
| LSD 5% | 13 | 23 | 1.3 | 2.1 | 12 | 8 |

[1]Plantings established in 1991 and 1993 and harvested for the subsequent two years.
[2]% Early harvest = % of total crop harvested from 6/15/92 to 6/24/92 (full season 6/15/92 to 7/15/92); 6/21/93 to 6/28/93 (full season 6/21/93 to 7/19/93); 6/08/94 to 6/15/94 (full season 6/08/94 to 7/05/94); and 6/19/95 to 6/23/95 (full season 6/19/95 to 7/06/95.
[3]% Stand was evaluated during June of each year.
[4]Vigor was rated on a scale of 1 to 9 with 9 being very vigorous.
[5]Winter stand loss was the difference between % stand in June and % stand in October of the previous year.

TABLE 3

Performance of strawberry cultivars at the University of Minnesota Horticultural Research Center, Excelsior, Minnesota in 1992, 1994, and 1995.[1]

| Cultivar | 1992 | 1994 | 1995 |
|---|---|---|---|
| | Yield (1000 lb/A) | | |
| Earliglow | n.a. | 6.5 | 9.5 |
| Veestar | 9.1 | 10.4 | 9.9 |
| Annapolis | 7.1 | 8.8 | 10.2 |
| Honeoye | 12.9 | 10.4 | 9.5 |
| Chambly | n.a. | 8.5 | 13.2 |
| Redcoat | 8.7 | n.a. | n.a. |
| MNUS 248 | 14.8 | 19.4 | 15.8 |

TABLE 3-continued

Performance of strawberry cultivars at the University of Minnesota Horticultural Research Center, Excelsior, Minnesota in 1992, 1994, and 1995.[1]

| Cultivar | 1992 | 1994 | 1995 |
|---|---|---|---|
| Glooscap | 4.6 | 13.1 | 14.0 |
| Kent | 8.1 | 14.2 | 10.8 |
| Cavendish | 5.5 | 15.4 | 16.2 |
| Jewel | 5.2 | 12.7 | 12.1 |
| Seneca | n.a. | 10.7 | 9.8 |
| Startyme | n.a. | 8.6 | 6.5 |
| Blomidon | 6.6 | 7.3 | 6.7 |
| MNUS 210 | 5.8 | 11.7 | 14.7 |
| Lateglow | 6.5 | 9.3 | 9.0 |
| Bounty | 6.5 | n.a. | n.a. |
| LSD 5% | 3.3 | 3.5 | 2.7 |
| | | Berry weight (g) | |
| Earliglow | n.a. | 9.7 | 9.1 |
| Veestar | 7.5 | 9.1 | 8.0 |
| Annapolis | 17.4 | 14.8 | 8.9 |
| Honeoye | 14.1 | 9.1 | 7.5 |
| Chambly | n.a. | 9.3 | 7.9 |
| Redcoat | 11.2 | n.a. | n.a. |
| MNUS 248 | 15.5 | 11.0 | 9.5 |
| Glooscap | 10.6 | 10.0 | 7.3 |
| Kent | 16.3 | 9.6 | 8.6 |
| Cavendish | 15.0 | 12.2 | 10.5 |
| Jewel | 12.9 | 12.8 | 10.8 |
| Seneca | n.a. | 11.9 | 9.8 |
| Startyme | n.a. | 12.0 | 11.8 |
| Blomidon | 11.8 | 9.5 | 10.2 |
| MNUS 210 | 17.5 | 14.0 | 13.2 |
| Lateglow | 14.4 | 11.5 | 11.2 |
| Bounty | 10.0 | n.a. | n.a. |
| LSD 5% | 3.1 | 1.3 | 1.1 |
| | | % Early harvest[2] | |
| Earliglow | n.a. | 66 | 55 |
| Veestar | 58 | 61 | 69 |
| Annapolis | 94 | 57 | 49 |
| Honeoye | 64 | 51 | 67 |
| Chambly | n.a. | 36 | 55 |
| Redcoat | 71 | n.a. | n.a. |
| MNUS 248 | 57 | 14 | 26 |
| Glooscap | 60 | 15 | 34 |
| Kent | 63 | 29 | 47 |
| Cavendish | 52 | 27 | 20 |
| Jewel | 79 | 26 | 25 |
| Seneca | n.a. | 32 | 47 |
| Startyme | n.a. | 15 | 24 |
| Blomidon | 37 | 15 | 22 |
| MNUS 210 | 52 | 4 | 22 |
| Lateglow | 35 | 3 | 0 |
| Bounty | 18 | n.a. | n.a. |
| LSD 5% | 22 | 14 | 12 |
| | | Stand (%)[3] | |
| Earliglow | n.a. | 65 | 78 |
| Veestar | 78 | 80 | 90 |
| Annapolis | 80 | 65 | 73 |
| Honeoye | 83 | 65 | 65 |
| Chambly | n.a. | 63 | 73 |
| Redcoat | 75 | n.a. | n.a. |
| MNUS 248 | 70 | 85 | 80 |
| Glooscap | 58 | 70 | 85 |
| Kent | 65 | 68 | 73 |
| Cavendish | 63 | 55 | 75 |
| Jewel | 58 | 68 | 73 |
| Seneca | n.a. | 70 | 65 |
| Startyme | n.a. | 60 | 70 |
| Blomidon | 68 | 60 | 68 |
| MNUS 210 | 68 | 68 | 83 |
| Lateglow | 75 | 70 | 83 |
| Bounty | 75 | n.a. | n.a. |
| LSD 5% | 18 | 17.86 | 11.21 |

TABLE 3-continued

Performance of strawberry cultivars at the University of Minnesota Horticultural Research Center, Excelsior, Minnesota in 1992, 1994, and 1995.[1]

| Cultivar | 1992 | 1994 | 1995 |
|---|---|---|---|
| | | Vigor[4] | |
| Earliglow | n.a. | 7.5 | 8.8 |
| Veestar | 7.0 | 7.3 | 8.3 |
| Annapolis | 8.0 | 6.8 | 7.3 |
| Honeoye | 8.3 | 6.5 | 5.8 |
| Chambly | n.a. | 7.3 | 7.5 |
| Redcoat | 8.0 | n.a. | n.a. |
| MNUS 248 | 6.0 | 7.3 | 6.5 |
| Glooscap | 6.5 | 7.3 | 7.3 |
| Kent | 8.0 | 6.3 | 7.0 |
| Cavendish | 7.0 | 7.0 | 8.0 |
| Jewel | 6.8 | 8.0 | 8.0 |
| Seneca | n.a. | 6.8 | 7.5 |
| Startyme | n.a. | 7.0 | 7.5 |
| Blomidon | 7.3 | 6.3 | 6.8 |
| MNUS 210 | 7.5 | 7.0 | 8.0 |
| Lateglow | 7.8 | 7.0 | 8.0 |
| Bounty | 7.8 | n.a. | n.a. |
| LSD 5% | 1.1 | 1.1 | 1.0 |

[1]Plantings established in 1991 and 1993 and harvested in the subsequent one or two years, respectively.
[2]% Early harvest = % of total crop harvested from 6/11/92 to 6/16/92 (full season 6/11/92 to 7/02/92); 6/14/94 to 6/17/94 (full season 6/14/94 to 7/05/94) and 6/16/95 to 6/23/95 (full season 6/16/95 to 7/06/95).
[3]% Stand was evaluated during June of each year.
[4]Vigor was rated on a scale of 1 to 9 with 9 being very vigorous.

TABLE 4

Performance of strawberry cultivars in Minnesota in 1996.[1]

| Cultivar | Gr. Rapids Mulched 1996 | Gr. Rapids Un-mulched 1996 | Morris 1996 | Excelsior 1996 |
|---|---|---|---|---|
| | | Yield (1000 lb/A) | | |
| Annapolis | 4.2 | 4.8 | 9.7 | 5.7 |
| Honeoye | 9.2 | 11.2 | 10.9 | 6.0 |
| MNUS 248 | 19.9 | 16.8 | 20.6 | 12.5 |
| Glooscap | 11.1 | 13.9 | 8.5 | 7.6 |
| Kent | 13.7 | 14.7 | 13.2 | 6.7 |
| Cavendish | 10.1 | 12.4 | 12.7 | 8.2 |
| Jewel | 6.4 | 10.2 | 14.9 | 5.8 |
| Mira | 8.6 | 9.2 | 14.5 | 9.7 |
| Startyme | 4.1 | 3.9 | 6.1 | 2.9 |
| MNUS 210 | 10.7 | 10.6 | 15.8 | 9.6 |
| Lateglow | 5.5 | 7.1 | 11.0 | 6.3 |
| LSD 5% | 3.6 | 2.7 | 3.7 | 2.3 |
| | | Berry weight (g) | | |
| Annapolis | 13.6 | 13.6 | 10.2 | 12.2 |
| Honeoye | 12.9 | 11.8 | 9.5 | 10.7 |
| MNUS 248 | 15.4 | 14.9 | 9.8 | 10.9 |
| Glooscap | 13.3 | 12.9 | 8.2 | 9.8 |
| Kent | 14.2 | 14.5 | 8.9 | 9.9 |
| Cavendish | 17.0 | 16.2 | 11.9 | 11.5 |
| Jewel | 13.8 | 13.2 | 10.5 | 11.2 |
| Mira | 13.6 | 13.9 | 9.4 | 10.6 |
| Startyme | 12.8 | 12.4 | 8.6 | 8.0 |
| MNUS 210 | 18.5 | 18.2 | 11.8 | 12.9 |
| Lateglow | 13.5 | 14.1 | 8.1 | 10.1 |
| LSD 5% | 1.4 | 1.4 | 1.0 | 1.4 |
| | | % Early harvest[2] | | |
| Annapolis | 41 | 62 | 74 | 85 |
| Honeoye | 35 | 47 | 69 | 81 |

TABLE 4-continued

Performance of strawberry cultivars in Minnesota in 1996.[1]

| Cultivar | Gr. Rapids Mulched 1996 | Gr. Rapids Un-mulched 1996 | Morris 1996 | Excelsior 1996 |
|---|---|---|---|---|
| MNUS 248 | 21 | 20 | 48 | 35 |
| Glooscap | 15 | 17 | 70 | 56 |
| Kent | 23 | 23 | 44 | 57 |
| Cavendish | 19 | 20 | 36 | 40 |
| Jewel | 11 | 21 | 32 | 49 |
| Mira | 14 | 20 | 40 | 45 |
| Startyme | 8 | 15 | 44 | 44 |
| MNUS 210 | 1 | 5 | 34 | 23 |
| Lateglow | 1 | 5 | 26 | 30 |
| LSD 5% | 8 | 9 | 12 | 14 |
| | | Stand (%)[3] | | |
| Annapolis | 73 | 79 | 80 | 63 |
| Honeoye | 90 | 93 | 75 | 65 |
| MNUS 248 | 91 | 88 | 83 | 73 |
| Glooscap | 89 | 90 | 63 | 70 |
| Kent | 91 | 93 | 73 | 53 |
| Cavendish | 86 | 91 | 73 | 70 |
| Jewel | 90 | 96 | 85 | 65 |
| Mira | 94 | 92 | 80 | 70 |
| Startyme | 76 | 77 | 62 | 68 |
| MNUS 210 | 95 | 86 | 80 | 80 |
| Lateglow | 88 | 86 | 83 | 65 |
| LSD 5% | 14 | 11 | 12 | 11 |
| | | Vigor[4] | | |
| Annapolis | 8.8 | 9.0 | 6.3 | 7.3 |
| Honeoye | 9.0 | 9.0 | 7.3 | 7.3 |
| MNUS 248 | 8.5 | 8.7 | 5.8 | 6.3 |
| Glooscap | 9.0 | 8.0 | 6.0 | 7.8 |
| Kent | 8.9 | 8.9 | 5.8 | 6.8 |
| Cavendish | 8.5 | 8.7 | 6.8 | 7.3 |
| Jewel | 9.0 | 9.0 | 8.3 | 7.5 |
| Mira | 8.9 | 9.0 | 7.0 | 8.3 |
| Startyme | 9.0 | 6.8 | 6.7 | 6.3 |
| MNUS 210 | 9.0 | 9.0 | 7.3 | 8.5 |
| Lateglow | 8.0 | 8.9 | 7.5 | 7.0 |
| LSD 5% | 0.4 | 0.4 | 1.0 | 1.0 |
| | | Winter stand loss (%) | | |
| Annapolis | | | −3 | −8 |
| Honeoye | | | −10 | −3 |
| MNUS 248 | | | −8 | −3 |
| Glooscap | | | −10 | 0 |
| Kent | | | −10 | −13 |
| Cavendish | | | −8 | −5 |
| Jewel | | | −10 | −8 |
| Mira | | | −10 | −8 |
| Startyme | | | −14 | −15 |
| MNUS 210 | | | −8 | 3 |
| Lateglow | | | −3 | −10 |
| LSD 5% | | | 9 | 13 |

[1]Plantings established in 1995.

[2]% Early harvest = % of total crop harvested from 6/28 to 7/05 (full season to 7/26/96) at Grand Rapids; from 6/21 to 7/1 (full season to 7/17/96) at Morris and from 6/28/96 to 7/1 (full season to 7/16/96) at Excelsior.

[3]% Stand was evaluated during June of each year.

[4]Vigor rated from 1 (very low) to 9 (very high).

[5]Winter stand loss was the difference between % stand in June and % stand in October of the previous year.

TABLE 5

Fruit quality ratings of strawberry cultivars at the North Central Experiment Station, Grand Rapids, Minnesota in trials from 1992–1995.[1]

| Cultivar | Appearance[2] | | Skin color[2] | | Flesh color[2] | |
|---|---|---|---|---|---|---|
| | 1992 | 1993 | 1992 | 1993 | 1992 | 1993 |
| Veestar | 6.5 | 5.3 | 7.5 | 6.3 | 8.0 | 8.0 |
| Annapolis | 7.5 | 7.8 | 8.0 | 8.0 | 8.0 | 7.7 |
| Honeoye | 7.0 | 7.7 | 7.0 | 8.0 | 7.5 | 8.0 |
| MNUS 248 | 7.5 | 8.0 | 7.5 | 8.2 | 8.0 | 8.3 |
| Glooscap | 8.0 | 8.3 | 8.5 | 8.5 | 8.5 | 8.3 |
| Kent | 8.0 | 8.0 | 8.0 | 8.2 | 8.0 | 8.0 |
| Cavendish | 7.5 | 7.7 | 8.0 | 8.0 | 8.0 | 7.8 |
| Northland | 7.0 | 7.7 | 7.0 | 7.7 | 8.0 | 8.3 |
| Trumpeter | 7.5 | 7.7 | 8.0 | 8.0 | 8.5 | 8.3 |
| Blomidon | 7.5 | 7.3 | 8.0 | 7.3 | 8.5 | 7.8 |
| MNUS 210 | 7.5 | 7.7 | 7.0 | 7.7 | 8.0 | 7.7 |
| Lateglow | 8.0 | 7.7 | 7.5 | 7.5 | 7.0 | 8.0 |
| Bounty | 7.0 | 8.0 | 6.5 | 8.2 | 8.0 | 8.2 |
| | 1994 | 1995 | 1994 | 1995 | 1994 | 1995 |
| Earliglow | 7.0 | 7.0 | 8.0 | 7.0 | 8.0 | 8.0 |
| Veestar | 6.5 | 6.0 | 6.5 | 7.8 | 7.5 | 7.3 |
| Annapolis | 7.0 | 6.5 | 6.0 | 6.5 | 7.0 | 7.5 |
| Honeoye | 8.0 | 7.5 | 8.0 | 8.0 | 8.0 | 8.0 |
| Chambly | 8.0 | 6.5 | 8.0 | 7.0 | 8.0 | 7.5 |
| MNUS 248 | 8.0 | 8.0 | 8.0 | 8.0 | 8.0 | 8.3 |
| Glooscap | 8.0 | 7.8 | 8.0 | 8.0 | 8.5 | 8.5 |
| Kent | 8.0 | 6.7 | 8.0 | 7.3 | 8.0 | 6.3 |
| Cavendish | 7.5 | 6.0 | 8.5 | 7.5 | 8.0 | 8.5 |
| Jewel | 8.0 | 7.3 | 8.0 | 7.7 | 8.0 | 7.7 |
| Seneca | 6.0 | 7.0 | 7.5 | 7.5 | 8.0 | 7.5 |
| MNUS 210 | 6.5 | 7.0 | 7.0 | 7.0 | 7.0 | 7.0 |
| Blomidon | 7.5 | 5.5 | 8.5 | 6.5 | 8.0 | 8.0 |
| Lateglow | 8.0 | 7.0 | 6.5 | 7.0 | 8.0 | 6.7 |

| Cultivar | Firmness[2] | | Flavor[2] | | Overall fruit quality[2] | |
|---|---|---|---|---|---|---|
| | 1992 | 1993 | 1992 | 1993 | 1992 | 1993 |
| Veestar | 6.0 | 5.7 | 6.5 | 5.7 | 6.0 | 5.3 |
| Annapolis | 7.0 | 7.5 | 7.5 | 7.0 | 7.5 | 6.2 |
| Honeoye | 6.5 | 6.7 | 6.5 | 6.0 | 7.0 | 6.8 |
| MNUS 248 | 7.5 | 7.3 | 8.0 | 7.0 | 7.5 | 8.0 |
| Glooscap | 7.0 | 6.8 | 7.0 | 7.5 | 7.5 | 7.7 |
| Kent | 6.5 | 7.2 | 7.0 | 6.7 | 8.0 | 8.2 |
| Cavendish | 7.0 | 7.5 | 7.5 | 7.0 | 8.0 | 8.0 |
| Northland | 5.0 | 5.3 | 6.5 | 6.3 | 7.0 | 6.7 |
| Trumpeter | 6.0 | 5.3 | 7.0 | 5.7 | 7.0 | 6.3 |
| Blomidon | 8.0 | 6.3 | 6.5 | 6.3 | 6.5 | 6.5 |
| MNUS 210 | 8.0 | 7.7 | 7.5 | 7.3 | 7.5 | 7.5 |
| Lateglow | 8.0 | 7.5 | 7.5 | 7.5 | 8.0 | 7.7 |
| Bounty | 6.0 | 6.2 | 7.0 | 6.7 | 6.5 | 7.5 |
| | 1994 | 1995 | 1994 | 1995 | 1994 | 1995 |
| Earliglow | 7.0 | 7.5 | 7.5 | 6.5 | 7.0 | 6.5 |
| Veestar | 5.5 | 6.0 | 6.0 | 6.0 | 6.0 | 6.0 |
| Annapolis | 7.0 | 6.5 | 7.0 | 7.0 | 7.0 | 6.5 |
| Honeoye | 6.5 | 6.7 | 7.0 | 6.8 | 7.0 | 7.0 |
| Chambly | 7.0 | 7.0 | 6.5 | 5.5 | 6.5 | 6.0 |
| MNUS 248 | 7.5 | 7.3 | 7.0 | 7.0 | 7.5 | 7.7 |
| Glooscap | 7.0 | 7.0 | 6.5 | 7.5 | 8.0 | 8.0 |
| Kent | 6.5 | 6.7 | 6.0 | 6.7 | 7.5 | 6.7 |
| Cavendish | 7.5 | 6.3 | 7.5 | 8.0 | 8.0 | 7.0 |
| Jewel | 7.0 | 7.0 | 7.5 | 7.0 | 7.5 | 6.7 |
| Seneca | 7.5 | 8.0 | 6.5 | 6.5 | 6.5 | 6.5 |
| MNUS 210 | 7.0 | 7.5 | 6.0 | 7.5 | — | 8.0 |
| Blomidon | 7.0 | 8.0 | 5.0 | 6.5 | — | 5.5 |
| Lateglow | 7.0 | 7.0 | 7.0 | 7.0 | 8.0 | 7.0 |

[1]Plantings were established in 1991 and 1993 and evaluated for the subsequent two years.

[2]Appearance, Firmness, Skin toughness, Flavor, and Overall fruit quality are rated on a scale of 1 to 9 with 9 being best.

TABLE 6

Fruit quality of strawberry selections at Grand Rapids, Minnesota in 1996.[1,2]

| Selection | Symmetry | Appearance | Skin color | Flesh color | Firmness | Flavor | Overall rating[3] |
|---|---|---|---|---|---|---|---|
| Annapolis | 7.0 | 7.3 | 7.0 | 8.0 | 7.5 | 7.3 | 3.0 |
| Honeoye | 7.5 | 7.8 | 8.0 | 8.5 | 7.0 | 6.5 | 3.0 |
| MNUS 248 | 7.5 | 8.0 | 8.0 | 8.5 | 7.0 | 7.8 | 3.5 |
| Glooscap | 7.5 | 8.0 | 8.0 | 8.5 | 7.0 | 7.0 | 3.3 |
| Kent | 7.5 | 7.5 | 8.0 | 7.5 | 7.5 | 7.3 | 3.3 |
| Cavendish | 7.5 | 7.0 | 6.5 | 8.5 | 7.5 | 8.0 | 2.8 |
| Jewel | 7.5 | 8.0 | 8.0 | 8.5 | 7.0 | 7.5 | 3.5 |
| Mira | 6.5 | 7.0 | 7.5 | 6.0 | 7.0 | 6.5 | 2.8 |
| Startyme | 7.0 | 6.0 | 7.0 | 6.0 | 8.0 | 7.0 | 2.0 |
| MNUS 210 | 7.0 | 7.5 | 8.0 | 7.5 | 7.5 | 7.5 | 3.3 |
| Lateglow | 8.0 | 8.0 | 8.0 | 7.5 | 7.5 | 7.5 | 3.5 |

[1]Average of fruit ratings from 6/10/96 and 6/12/96.
[2]All ratings except overall quality are on a 1 to 9 scale with 9 being best.
[3]Overall quality is rated on a scale from 1 to 5 with 5 being best.

TABLE 7

Fruit quality ratings of strawberry cultivars at the West Central Experiment Station, Morris, Minnesota in 1992–1995.[1]

| Cultivar | Appearance[2] | | Firmness[2] | | Skin toughness[2] | |
|---|---|---|---|---|---|---|
| | 1992 | 1993 | 1992 | 1993 | 1992 | 1993 |
| Veestar | 7.0 | 7.0 | 6.0 | 6.0 | 7.0 | 6.0 |
| Annapolis | 8.0 | 7.0 | 8.0 | 8.0 | 8.0 | 7.0 |
| Honeoye | 7.0 | 8.0 | 7.0 | 7.0 | 8.0 | 6.0 |
| Redcoat | 6.0 | 7.0 | 6.0 | 6.0 | 7.0 | 6.0 |
| MNUS 248 | 7.5 | 7.0 | 7.0 | 7.0 | 6.0 | 7.0 |
| Glooscap | 8.0 | 8.0 | 7.0 | 7.0 | 7.0 | 6.0 |
| Kent | 7.0 | 8.0 | 7.0 | 7.0 | 6.0 | 7.0 |
| Cavendish | 6.0 | 7.0 | 8.0 | 8.0 | 6.0 | 6.0 |
| Jewel | n.a. | 7.0 | n.a. | 7.0 | n.a. | 8.0 |
| Trumpeter | 6.0 | 7.0 | 6.0 | 6.0 | 5.0 | 5.0 |
| MNUS 210 | 8.0 | 8.0 | 9.0 | 8.0 | 7.0 | 8.0 |
| Blomidon | 8.0 | 9.0 | 7.0 | 8.0 | 7.0 | 8.0 |
| Bounty | 7.0 | 7.0 | 6.0 | 7.0 | 7.0 | 7.0 |
| Lateglow | 8.0 | 8.0 | 8.0 | 7.0 | 6.0 | 7.0 |
| | 1994 | 1995 | 1994 | 1995 | 1994 | 1995 |
| Veestar | 6.5 | 5.0 | 6.0 | 5.0 | 5.0 | 5.0 |
| Earliglow | 6.5 | 7.0 | 7.0 | 7.5 | 6.0 | 7.0 |
| Annapolis | 8.0 | 7.0 | 7.0 | 8.0 | 7.0 | 7.0 |
| Honeoye | 6.5 | 6.0 | 6.0 | 7.0 | 6.0 | 6.0 |
| Chambly | 7.0 | 6.0 | 7.0 | 7.0 | 7.0 | 8.0 |
| MNUS 248 | 8.0 | 7.0 | 7.0 | 7.5 | 5.0 | 7.0 |
| Glooscap | 7.5 | 6.0 | 7.0 | 7.0 | 6.0 | 7.0 |
| Kent | 7.5 | 7.0 | 7.0 | 7.0 | 6.0 | 7.0 |
| Cavendish | 7.5 | 6.5 | 7.0 | 7.5 | 7.0 | 7.5 |
| Jewel | 8.0 | 8.0 | 7.0 | 8.0 | 7.0 | 8.0 |
| Seneca | 8.0 | 8.0 | 8.0 | 8.0 | 7.0 | 7.0 |
| Blomidon | 7.5 | 8.0 | 8.0 | 7.5 | 8.0 | 7.0 |
| Lateglow | 7.0 | 7.0 | 6.0 | 7.0 | 6.0 | 7.5 |
| MNUS 210 | 7.0 | 7.5 | 8.0 | 8.0 | 8.0 | 8.0 |

| Cultivar | Flavor[2] | | Overall fruit quality[3] | |
|---|---|---|---|---|
| | 1992 | 1993 | 1992 | 1993 |
| Veestar | 7.0 | 7.0 | 2.0 | 2.0 |
| Annapolis | 7.0 | 7.5 | 3.0 | 3.5 |
| Honeoye | 6.0 | 6.0 | 2.5 | 3.0 |
| Redcoat | 7.0 | 6.0 | 2.0 | 2.5 |
| MNUS 248 | 7.0 | 6.0 | 2.0 | 2.5 |
| Glooscap | 7.0 | 7.0 | 2.5 | 2.5 |
| Kent | 6.0 | 6.0 | 2.0 | 3.5 |
| Cavendish | 7.0 | 7.0 | 3.0 | 2.0 |

TABLE 7-continued

Fruit quality ratings of strawberry cultivars at the West Central Experiment Station, Morris, Minnesota in 1992–1995.[1]

| | | | | |
|---|---|---|---|---|
| Jewel | n.a. | 8.0 | n.a. | 3.0 |
| Trumpeter | 7.0 | 6.0 | 2.0 | 2.0 |
| MNUS 210 | 7.0 | 8.0 | 3.5 | 4.0 |
| Blomidon | 7.0 | 7.0 | 3.0 | 4.0 |
| Bounty | 8.0 | 7.0 | 2.5 | 2.5 |
| Lateglow | 7.0 | 7.5 | 3.0 | 3.5 |
| | 1994 | 1995 | 1994 | 1995 |
| Veestar | 7.0 | 8.0 | 2.0 | 2.0 |
| Earliglow | 6.0 | 8.0 | 2.0 | 3.0 |
| Annapolis | 7.0 | 7.5 | 3.5 | 3.0 |
| Honeoye | 7.0 | 7.0 | 2.0 | 2.0 |
| Chambly | 6.0 | 6.5 | 2.5 | 2.5 |
| MNUS 248 | 7.0 | 7.0 | 2.5 | 3.0 |
| Glooscap | 7.0 | 7.0 | 3.0 | 2.5 |
| Kent | 7.0 | 3.5 | 3.0 | 2.5 |
| Cavendish | 7.5 | 7.0 | 3.5 | 3.0 |
| Jewel | 6.5 | 7.5 | 3.0 | 3.5 |
| Seneca | 7.5 | 7.0 | 3.5 | 3.5 |
| Blomidon | 7.5 | 7.0 | 3.5 | 3.0 |
| Lateglow | 7.0 | 7.0 | 2.5 | 2.5 |
| MNUS 210 | 7.0 | 8.0 | 2.5 | 3.5 |

[1]Plantings established in 1991 and 1993, and evaluated in the subsequent two years.
[2]Appearance, Firmness, Skin toughness, and Flavor are rated on a scale of 1 to 9 with 9 being best.
[3]Overall fruit quality is rated on a scale of 1 to 5 with 5 being best.

TABLE 8

Fruit quality ratings of strawberry cultivars at the University of Minnesota Horticultural Research Center, Excelsior, Minnesota in 1992 and 1994.[1]

| Cultivar | Appearance[2] | | Firmness[2] | | Skin toughness[2] | |
|---|---|---|---|---|---|---|
| | 1992 | 1994 | 1992 | 1994 | 1992 | 1994 |
| Earliglow | n.a. | 8.0 | n.a. | 7.0 | n.a. | 7.0 |
| Veestar | 6.5 | 7.0 | 4 | 6.0 | 5 | 6.0 |
| Annapolis | 9 | 8.0 | 8 | 7.0 | 7 | 8.0 |
| Redcoat | 8 | n.a. | 6 | n.a. | 6 | n.a. |
| Honeoye | 8 | 7.0 | 6 | 7.0 | 6 | 6.0 |
| Chambly | n.a. | 7.0 | n.a. | 7.0 | n.a. | 7.0 |
| MNUS 248 | 7 | 8.0 | 7 | 7.0 | 6 | 6.0 |
| Glooscap | 7.5 | 6.0 | 6 | 7.0 | 6 | 7.0 |
| Kent | 8.5 | 8.0 | 8 | 7.0 | 7 | 6.0 |
| Cavendish | 7.5 | 8.0 | 8 | 7.0 | 8 | 7.0 |
| Jewel | 9 | 8.0 | 8 | 7.0 | 7 | 8.0 |
| Seneca | n.a. | 8.0 | n.a. | 8.0 | n.a. | 7.0 |
| MNUS 210 | 7 | 8.0 | 8 | 8.0 | 8 | 8.0 |
| Blomidon | 8.5 | 8.0 | 8 | 7.0 | 8 | 7.0 |
| Lateglow | 7.5 | 6.0 | 7 | 8.0 | 8 | 7.0 |
| Bounty | 6.5 | n.a. | 6 | n.a. | 5 | n.a. |
| Startyme | n.a. | 7.0 | n.a. | 8.0 | n.a. | 8.0 |

| Cultivar | Flavor[2] | | Overall fruit quality[3] | |
|---|---|---|---|---|
| | 1992 | 1994 | 1992 | 1994 |
| Earliglow | n.a. | 8.0 | n.a. | 3.0 |
| Veestar | 7 | 7.0 | 1.0 | 2.0 |
| Annapolis | 7 | 7.0 | 4.0 | 3.5 |
| Redcoat | 6 | n.a. | 2.0 | n.a. |
| Honeoye | 7 | 7.0 | 3.0 | 2.5 |
| Chambly | n.a. | 7.0 | n.a. | 2.5 |
| MNUS 248 | 8 | 7.0 | 3.0 | 2.5 |
| Glooscap | 7 | 7.0 | 3.0 | 3.0 |
| Kent | 7 | 7.0 | 4.0 | 3.0 |
| Cavendish | 8 | 7.0 | 4.0 | 3.0 |

TABLE 8-continued

Fruit quality ratings of strawberry cultivars at the University of Minnesota Horticultural Research Center, Excelsior, Minnesota in 1992 and 1994.[1]

| | | | | |
|---|---|---|---|---|
| Jewel | 7 | 7.0 | 4.0 | 4.0 |
| Seneca | n.a. | 7.0 | n.a. | 3.0 |
| MNUS 210 | 7 | 8.0 | 3.0 | 3.0 |
| Blomidon | 7 | 7.0 | 4.0 | 3.0 |
| Lateglow | 8 | 7.0 | 4.0 | 2.5 |
| Bounty | 7 | n.a. | 2.0 | n.a. |
| Startyme | n.a. | 9.0 | n.a. | 3.5 |

[1]Plantings established in 1991 and 1993 were evaluated in 1992 and 1994, respectively.
[2]Appearance, Firmness, Skin toughness, and Flavor are rated on a scale of 1 to 9 with 9 being best.
[3]Overall fruit quality is rated on a scale of 1 to 5 with 5 being best.

TABLE 9

Fruit quality of strawberry selections at Morris and Excelsior, Minnesota in 1996.[1,2]

| | Appearance | | Firmness | | Skin toughness | |
|---|---|---|---|---|---|---|
| Cultivar | Morris | Ex-celsior | Morris | Ex-celsior | Morris | Ex-celsior |
| Annapolis | 7.3 | 7.5 | 7.5 | 8.0 | 7.5 | 7.0 |
| Honeoye | 7.0 | 7.5 | 7.0 | 7.0 | 6.5 | 7.0 |
| MNUS 248 | 8.0 | 8.0 | 8.0 | 8.0 | 6.5 | 7.0 |
| Glooscap | 7.3 | 7.0 | 7.0 | 7.0 | 8.0 | 8.0 |
| Kent | 8.0 | 7.5 | 7.0 | 8.0 | 6.5 | 6.0 |
| Cavendish | 6.5 | 7.5 | 8.0 | 8.0 | 6.5 | 8.0 |
| Jewel | 7.5 | 7.0 | 7.0 | 8.0 | 7.0 | 7.0 |
| Mira | 7.5 | 9.0 | 7.0 | 7.0 | 7.5 | 8.0 |
| Startyme | 7.0 | 6.0 | 8.0 | 9.0 | 7.0 | 9.0 |
| MNUS 210 | 7.5 | 7.0 | 8.0 | 8.0 | 6.5 | 8.0 |
| Lateglow | 7.8 | 8.0 | 7.0 | 7.0 | 8.0 | 7.0 |

| | Flavor | | Overall fruit quality[3] | |
|---|---|---|---|---|
| | Morris | Excelsior | Morris | Excelsior |
| Annapolis | 7.0 | 6.5 | 3.5 | 3.0 |
| Honeoye | 6.0 | 7.0 | 2.3 | 3.0 |
| MNUS 248 | 7.3 | 7.0 | 3.5 | 3.5 |
| Glooscap | 7.0 | 6.0 | 3.0 | 2.5 |
| Kent | 6.5 | 7.0 | 3.0 | 3.0 |
| Cavendish | 6.3 | 7.0 | 2.5 | 3.0 |
| Jewel | 7.0 | 8.0 | 3.3 | 3.0 |
| Mira | 6.0 | 6.0 | 3.5 | 3.0 |
| Startyme | | 6.0 | | 2.5 |
| MNUS 210 | 8.0 | 8.0 | 3.5 | 3.0 |
| Lateglow | 7.0 | 7.5 | 3.0 | 3.0 |

[1]Plantings established in 1995.
[2]All ratings except overall quality are on a 1 to 9 scale with 9 being best.
[3]Overall quality is rated on a scale from 1 to 5 with 5 being best.

TABLE 10

Disease responses of strawberry cultivars at the Univ. of Minnesota North Central Experiment Station, Grand Rapids, Minnesota in 1992 and 1993.[1]

| Cultivar | Leaf spot | | Powdery mildew | |
|---|---|---|---|---|
| | 1992 | 1993 | 1992 | 1993 |
| Veestar | 6.2 | 6.0 | 4.5 | 4.5 |
| Annapolis | 6.0 | 6.2 | 4.7 | 4.7 |
| Honeoye | 5.2 | 5.7 | 5.2 | 5.0 |
| MNUS 248 | 5.7 | 5.0 | 5.0 | 5.5 |
| Glooscap | 6.0 | 6.5 | 6.0 | 5.2 |
| Kent | 4.5 | 5.0 | 7.0 | 6.2 |

TABLE 10-continued

Disease responses of strawberry cultivars at the Univ. of Minnesota North Central Experiment Station, Grand Rapids, Minnesota in 1992 and 1993.[1]

| Cultivar | Leaf spot | | Powdery mildew | |
|---|---|---|---|---|
| Cavendish | 6.0 | 6.0 | 4.5 | 4.7 |
| Northland | 5.2 | 5.5 | 3.7 | 3.7 |
| Trumpeter | 6.2 | 6.0 | 3.7 | 3.7 |
| MNUS 210 | 6.0 | 6.2 | 6.5 | 6.2 |
| Blomidon | 6.0 | 6.2 | 6.5 | 5.7 |
| Lateglow | 3.5 | 3.7 | 4.2 | 3.5 |
| Bounty | 5.5 | 5.2 | 6.2 | 6.2 |
| LSD 5% | 1.1 | 0.9 | 0.7 | 0.8 |
| | 1994 | 1995 | 1994 | 1995 |
| Earliglow | 7.5 | 7.3 | 5.8 | 5.7 |
| Veestar | 7.3 | 6.3 | 5.8 | 6.3 |
| Annapolis | 7.5 | 7.0 | 6.0 | 6.0 |
| Honeoye | 6.3 | 5.7 | 5.8 | 6.3 |
| Chambly | 7.5 | 6.7 | 5.3 | 5.0 |
| MNUS 248 | 5.5 | 6.0 | 6.5 | 7.0 |
| Glooscap | 7.8 | 5.0 | 7.5 | 7.0 |
| Kent | 4.5 | 5.0 | 7.8 | 7.0 |
| Cavendish | 6.3 | 7.0 | 5.8 | 5.7 |
| Jewel | 6.8 | 6.7 | 7.8 | 7.7 |
| Seneca | 7.0 | 5.7 | 7.8 | 7.7 |
| Blomidon | 7.5 | 7.7 | 7.0 | 8.0 |
| Lateglow | 5.3 | 3.7 | 5.3 | 4.7 |
| MNUS 210 | 7.8 | 7.0 | 7.5 | 7.7 |
| LSD 5% | 0.9 | 1.2 | 0.8 | 0.7 |

[1]Leaf spot and powdery mildew ratings are on a scale from 1 = very severe infection to 9 = no infection.

TABLE 11

Disease responses of strawberry cultivars at the University of Minnesota Horticultural Research Center, Excelsior, Minnesota in 1994 and 1995.[1,2]

| | Winter injury | Black root rot | Leaf scorch | | Powdery mildew |
|---|---|---|---|---|---|
| Cultivar | 1994 | 1995 | 1994 | 1995 | 1995 |
| Earliglow | 7.3 | 8.5 | 9.0 | 8.0 | 6.0 |
| Veestar | 7.3 | 8.3 | 8.0 | 8.3 | 7.0 |
| Annapolis | 7.3 | 6.5 | 8.0 | 8.5 | 7.3 |
| Honeoye | 7.0 | 4.3 | 7.0 | 5.8 | 8.0 |
| Chambly | 7.5 | 6.5 | 9.0 | 8.0 | 6.5 |
| MNUS 248 | 8.3 | 5.5 | 7.0 | 7.3 | 7.3 |
| Glooscap | 7.8 | 7.0 | 8.0 | 7.8 | 7.0 |
| Kent | 7.0 | 5.3 | 5.0 | 5.5 | 7.8 |
| Cavendish | 7.0 | 7.5 | 8.0 | 8.5 | 7.3 |
| Jewel | 6.5 | 6.8 | 8.0 | 7.3 | 7.5 |
| Startyme | 7.0 | 6.5 | 6.0 | 7.0 | 7.0 |
| Seneca | 6.8 | 5.8 | 8.0 | 6.5 | 8.0 |
| MNUS 210 | 6.5 | 7.5 | 8.0 | 7.3 | 7.0 |
| Blomidon | 7.3 | 5.5 | 8.0 | 7.5 | 8.0 |

TABLE 11-continued

Disease responses of strawberry cultivars at the University of Minnesota Horticultural Research Center, Excelsior, Minnesota in 1994 and 1995.[1,2]

| | Winter injury | Black root rot | Leaf scorch | | Powdery mildew |
|---|---|---|---|---|---|
| Cultivar | 1994 | 1995 | 1994 | 1995 | 1995 |
| Lateglow | 7.3 | 7.5 | 7.0 | 6.3 | 6.0 |
| LSD 5% | 0.7 | 1.7 | n.a. | 0.8 | 0.7 |

[1]Planting established in 1993.
[2]Winter injury, Black root rot, Leaf scorch, and Powdery mildew were rated on a scale from 1 = very severe infection to 9 = no infection.

TABLE 12

Disease reactions of strawberry selections in Minnesota in 1995–1996.[1,2]

| | Grand Rapids | | | | Morris | Excelsior |
|---|---|---|---|---|---|---|
| | Leaf spot | | Powdery Mildew | | Iron | Leaf |
| Cultivar | Fall 1995 | Summer 1996 | Fall 1995 | Summer 1996 | chlorosis 1996 | Scorch 1996 |
| Annapolis | 7.8 | 7.8 | 5.8 | 6.0 | 7.3 | 7.8 |
| Honeoye | 8.0 | 6.3 | 5.8 | 7.0 | 6.8 | 7.3 |
| MNUS 248 | 7.8 | 7.0 | 6.5 | 7.0 | 4.5 | 6.3 |
| Glooscap | 8.0 | 7.3 | 6.3 | 7.3 | 6.5 | 7.5 |
| Kent | 7.5 | 5.0 | 7.0 | 7.0 | 6.5 | 4.5 |
| Cavendish | 7.8 | 6.8 | 5.5 | 6.0 | 7.0 | 7.0 |
| Jewel | 8.0 | 7.0 | 6.0 | 7.0 | 7.8 | 7.0 |
| Mira | 7.8 | 6.0 | 5.8 | 6.8 | 6.8 | 7.5 |
| Startyme | 7.7 | 5.7 | 6.0 | 7.7 | 5.3 | 5.8 |
| MNUS 210 | 8.0 | 7.8 | 7.0 | 7.0 | 7.8 | 8.0 |
| Lateglow | 7.5 | 4.8 | 5.3 | 5.8 | 7.8 | 7.3 |
| LSD 5% | ns | 0.6 | 0.7 | 0.5 | 0.9 | 0.9 |

[1]Plantings established in 1995.
[2]Disease reactions reated on a scale from 1 (severe symptoms) to 9 (no symptoms).

TABLE 13

Responses of strawbery genotypes to red stele root rot screening with mix of Phytophthora fragariae races A-1, A-2, A-3, A-4, and A-6 by root-dip inoculation at Beltsville, Maryland, 1993–94.[1]

| | Replication mean root scores[2] | |
|---|---|---|
| Genotype | Range | Mean |
| MNUS 248 | 8.0–9.0 | 8.5 |
| Yaquina B (resistant standard) | 8.0–8.5 | 8.2 |
| Del Norte (intermediate standard) | 8.0–8.5 | 8.2 |
| Blakemore (susceptible standard) | 4.5–5.0 | 4.7 |

[1]From Galletta, Maas, and Enns, Strawberry cultivar and selection red stele screening at USDA-Beltsville in 1993–1994. Advances in Strawberry Research 13:40–43 (1994).
[2]Three replications with two-plant plots were scored for root injury with 1–3 being very susceptible, 4–5 being suceptible, 6–7 being tolerant, and 8–9 being resistant. Blakemore was significantly more susceptible than the other varieties at P = 0.05 using Duncan's Multiple Range Test for mean separation.

We claim:

1. A new and distinct variety of strawberry plant, substantially as illustrated and described, characterized by the combined characteristics of its mid-season of fruit ripening, high productivity or yield, excellent survival in cold temperatures and resistance to red stele root rot.

* * * * *